(12) United States Patent
Muto et al.

(10) Patent No.: US 9,149,180 B2
(45) Date of Patent: Oct. 6, 2015

(54) OPTICAL TOMOGRAPHIC IMAGING APPARATUS

(75) Inventors: Kenji Muto, Fujisawa (JP); Takeshi Kitamura, Utsunomiya (JP)

(73) Assignee: CANON KABUSHIKI KAISHA, Tokyo (JP)

(*) Notice: Subject to any disclaimer, the term of this patent is extended or adjusted under 35 U.S.C. 154(b) by 642 days.

(21) Appl. No.: 12/842,740

(22) Filed: Jul. 23, 2010

(65) Prior Publication Data

US 2011/0026035 A1    Feb. 3, 2011

(30) Foreign Application Priority Data

Jul. 28, 2009  (JP) ................. 2009-174928

(51) Int. Cl.
    *G01B 9/02*    (2006.01)
    *G01B 11/02*   (2006.01)
    *A61B 3/10*    (2006.01)
    (Continued)

(52) U.S. Cl.
    CPC .............. *A61B 3/102* (2013.01); *A61B 5/0066* (2013.01); *A61B 5/0073* (2013.01); *G01N 21/4795* (2013.01)

(58) Field of Classification Search
    CPC .... A61B 3/102; A61B 5/0073; A61B 5/0066; G01N 21/4795; G01B 9/02044; G01B 9/02008; G01B 9/02083; G01B 9/02072; G01B 9/02091
    USPC ................................. 356/479, 497
    See application file for complete search history.

(56) References Cited

U.S. PATENT DOCUMENTS 6,002,429 A       12/1999   Ochi et al.
2001/0012063 A1    8/2001   Maeda
(Continued)

FOREIGN PATENT DOCUMENTS

CN       1924633        3/2007
EP       1870028 A1    12/2007
(Continued)

OTHER PUBLICATIONS

Korean Office Action issued on Oct. 2, 2012 in corresponding application No. 10-2010-0071168.

(Continued)

*Primary Examiner* — Tarifur Chowdhury
*Assistant Examiner* — Sunghee Y Gray
(74) *Attorney, Agent, or Firm* — Carter, DeLuca, Farrell & Schmidt, LLP (57) ABSTRACT

An optical tomographic imaging apparatus is provided which includes a low-resolution mode for rough imaging and a high-resolution mode for obtaining detailed images. In particular, an optical tomographic imaging apparatus is provided which enables tomographic imaging during a high-resolution mode to be performed at higher speeds. An imaging apparatus according to the present invention captures an optical interference tomographic image based on a combined beam that combines a return beam from an object irradiated by a measuring beam and a reference beam corresponding to the measuring beam. The imaging apparatus according to the present invention further includes a beam diameter changing unit for changing a beam diameter of the measuring beam. Furthermore, the imaging apparatus according to the present invention includes a detection unit configured to detect the combined beam at a resolution according to the beam diameter.

12 Claims, 6 Drawing Sheets

(51) Int. Cl.
*A61B 5/00* (2006.01)
*G01N 21/47* (2006.01)

(56) References Cited

U.S. PATENT DOCUMENTS

| | | | |
|---|---|---|---|
| 2002/0048025 A1 | 4/2002 | Takanoka | |
| 2007/0076220 A1* | 4/2007 | Kawahara | 356/511 |
| 2007/0086011 A1 | 4/2007 | Toida | |
| 2009/0015842 A1* | 1/2009 | Leitgeb et al. | 356/456 |
| 2009/0091766 A1 | 4/2009 | Hirose | |
| 2009/0203964 A1 | 8/2009 | Shimizu et al. | |
| 2009/0262359 A1* | 10/2009 | Bajraszewski et al. | 356/454 |
| 2009/0285354 A1* | 11/2009 | Hirose et al. | 378/19 |
| 2010/0226553 A1* | 9/2010 | Suehira | 382/131 |
| 2012/0044455 A1* | 2/2012 | Hirose | 351/206 |

FOREIGN PATENT DOCUMENTS

| | | | | |
|---|---|---|---|---|
| JP | 2000-116653 A | | 4/2000 | |
| JP | 2002-174769 A | | 6/2002 | |
| JP | 2007-101250 A | | 4/2007 | |
| JP | 2010210267 | * | 3/2009 | G01N 21/17 |
| JP | 2010279861 | * | 5/2009 | A61B 3/10 |

OTHER PUBLICATIONS

Chinese Office Action for Application No. 201010237383.6 dated Mar. 28, 2012.

* cited by examiner

1024 PIXELS

▨ PIXELS TO USER FOR IMAGE CONSTRUCTION

FIG. 6B

512 PIXELS

☐ PIXELS NOT TO USER FOR IMAGE CONSTRUCTION

FIG. 6C

1024 PIXELS

FIG. 6D

683 PIXELS

FIG. 6E

341 PIXELS

▨ PIXELS TO READ    ☐ PIXELS NOT TO READ

OPTICAL TOMOGRAPHIC IMAGING APPARATUS

BACKGROUND OF THE INVENTION

1. Field of the Invention

The present invention relates to an optical tomographic imaging apparatus, and particularly to an optical tomographic imaging apparatus used in opthalmologic diagnosis and treatment and the like.

2. Description of the Related Art

Various opthalmologic devices that utilize optical devices are in use today.

For example, various devices such as an anterior ocular segment photographing device, a fundus camera, and a scanning laser opthalmoscope (SLO) are used as optical devices for observing the eye.

Among such optical devices, an optical tomographic imaging apparatus based on optical coherence tomography (hereinafter referred to as OCT) that utilizes multi-wavelength lightwave interference is capable of obtaining a high-resolution tomographic image of a sample.

OCTs are becoming indispensable opthalmologic devices at outpatient retina specialists.

According to the optical tomographic imaging apparatus described above, when a sample is irradiated with a measuring beam that is a low-coherence light, a backscattering light from the sample can be measured at high sensitivity by using an interference system.

In addition, by scanning the measuring beam on the sample, the optical tomographic imaging apparatus can obtain a high-resolution tomographic image.

Therefore, since an optical tomographic imaging apparatus is also capable of high-resolution tomographic imaging of a retina in a fundus of an eye to be inspected, optical tomographic imaging apparatuses are widely used in opthalmologic diagnosis and treatment of retinas.

In recent years, with opthalmologic optical tomographic imaging apparatuses, a transition is underway from conventional time domain optical coherence tomography to Fourier domain optical coherence tomography that enables imaging at higher speeds.

While information is acquired per a specific depth in an eye to be inspected in time domain optical coherence tomography, since Fourier domain optical coherence tomography collectively acquires information in a depth direction, high-speed imaging can be performed.

High-speed imaging enables the prevention of image blur and image loss due to ocular movement represented by involuntary eye movement.

On the other hand, conventionally, an optical apparatus is proposed in Japanese Patent Application Laid-Open No. 2002-174769 in order to satisfy both demands for higher resolution and for reductions in imaging time.

Specifically, an optical apparatus for observing the inside of a biological specimen is proposed which uses both OCT and OCM (optical coherence microscopy) as the situation demands.

The apparatus is configured to use OCT when verifying large structures in a biological specimen and to be switchable to OCM when further observing an attention area in the biological specimen at a higher resolution.

In doing so, since OCT and OCM significantly differ from each other in depth of focus (DOF), the apparatus is configured using a beam diameter conversion optical system so that beam diameters respectively corresponding to OCT having a small numerical aperture and OCM having a large numerical aperture can be set.

Accordingly, observations can be performed at a high S/N ratio.

In addition, Japanese Patent Application Laid-Open No. 2007-101250 proposes an optical tomographic imaging apparatus arranged such that high resolution is achieved by OCT itself due to Fourier domain optical coherence tomography.

The apparatus is arranged so that in order to compensate for a narrow depth of focus (DOF), an optical path length adjustment unit is used to move a focusing position of a measured object in a depth direction to obtain a plurality of images, and the plurality of images is combined to acquire high-resolution tomographic images of the measured object in a horizontal direction and an optical axis direction.

SUMMARY OF THE INVENTION

However, the apparatuses in the conventional examples described above have the following problems.

In Japanese Patent Application Laid-Open No. 2002-174769, since imaging is performed at high-resolution, OCT imaging is not performed when a beam diameter is increased.

Therefore, no consideration is given to issues in OCT imaging arising when a beam diameter of a measuring beam is increased while performing high-resolution imaging using a beam diameter conversion optical system.

In addition, Japanese Patent Application Laid-Open No. 2007-101250 fails to disclose methods for achieving a higher speed during image composition and therefore takes time to acquire a plurality of images and to combine images.

On the other hand, with opthalmologic diagnosis and the like with an optical tomographic imaging apparatus, there is a strong demand for reducing imaging time in order to alleviate the burden on subjects being tested. As described above, apparatuses in conventional examples do not consider methods for reducing imaging time when performing high-resolution tomographic imaging by OCT.

The present invention has been made in consideration of the problems described above, and an object thereof is to provide an optical tomographic imaging apparatus including a low-resolution mode for rough imaging and a high-resolution mode for obtaining detailed images and, in particular, an optical tomographic imaging apparatus that enables tomographic imaging during a high-resolution mode to be performed at higher speeds.

According to one aspect of the present invention, an optical tomographic imaging apparatus is provided which splits a light from a light source into a measuring beam and a reference beam, guides the measuring beam to an object and the reference beam to a reference mirror, detects a beam combining a return beam of the measuring beam reflected or scattered by the object and the reference beam reflected by the reference mirror, and performs tomographic imaging of the object. The optical tomographic imaging apparatus comprises: a beam diameter adjustment unit which adjusts a beam diameter of the measuring beam to be guided to the object; a detection unit which includes a spectroscopic unit, an image forming unit and an opto-electric conversion element array and which detects the combined beam; and a change unit which reads a signal from the opto-electric conversion element array based on a beam diameter adjusted by the beam diameter adjustment unit and changes a ratio of the number of pixels used for imaging to a wavelength bandwidth of the light source.

According to another aspect of the present invention, an imaging apparatus is provided which captures an optical interference tomographic image based on a combined beam that combines a return beam from an object irradiated by a measuring beam and a reference beam corresponding to the measuring beam. The imaging apparatus comprises: a beam diameter changing unit which changes a beam diameter of the measuring beam; and a detection unit which detects the combined beam at a resolution corresponding to the beam diameter.

According to still another aspect of the present invention, an imaging apparatus is provided which captures an optical interference tomographic image based on a combined beam that combines a return beam from an object irradiated by a measuring beam and a reference beam corresponding to the measuring beam. The imaging apparatus comprises: a beam diameter changing unit which changes a beam diameter of the measuring beam; a spectroscopic unit which separates the combined beam; a range changing unit which changes a range on which the separated beam is to be irradiated based according to the beam diameter; a detection unit which detects a light from the range changing unit; and an acquiring unit which acquires an optical interference tomographic image of the object based on an output signal of the range from the detection unit.

According to still another aspect of the present invention, an imaging method is provided which captures an optical interference tomographic image based on a combined beam that combines a return beam from an object irradiated by a measuring beam and a reference beam corresponding to the measuring beam. The imaging method comprises: changing a beam diameter of the measuring beam; and detecting the combined beam at a resolution corresponding to the beam diameter.

According to the present invention, an optical tomographic imaging apparatus including a low-resolution mode for rough imaging and a high-resolution mode for obtaining detailed images and, in particular, an optical tomographic imaging apparatus that enables tomographic imaging during a high-resolution mode to be performed at higher speeds can be realized.

Consequently, an optical tomographic imaging apparatus that enables tomographic imaging of a retina with a reduced burden on a subject during opthalmologic diagnosis and the like can be provided.

Further features of the present invention will become apparent from the following description of exemplary embodiments with reference to the attached drawings.

BRIEF DESCRIPTION OF THE DRAWINGS

FIGS. 1A and 1B are diagrams describing a configuration of optical systems of optical tomographic imaging apparatuses according to the first and second embodiments of the present invention, wherein FIG. 1A is a diagram describing the configuration of the first embodiment and FIG. 1B is a diagram describing the configuration of the second embodiment.

FIGS. 2A, 2B, 2C, 2D, 2E, 2F, 2G and 2H are diagrams describing the first embodiment of the present invention.

FIGS. 3A and 3B are diagrams describing operations of the line sensor according to the first embodiment, and FIGS. 3C and 3D are diagrams describing operations of the line sensor according to the second embodiment.

FIGS. 4A, 4B, 4C, 4D and 4E are diagrams describing a third embodiment of the present invention.

FIGS. 5A and 5B are diagrams describing the spectroscope according to the fourth embodiment, and FIGS. 5C and 5D are diagrams describing the spectroscope according to the fifth embodiment.

FIGS. 6A, 6B, 6C, 6D and 6E are diagrams describing operations of line sensors according to the fourth and fifth embodiments of the present invention. FIGS. 6A and 6B are diagrams describing operations of the line sensor according to the fourth embodiment, and FIGS. 6C and 6D are diagrams describing operations of the line sensor according to the fifth embodiment.

DESCRIPTION OF THE EMBODIMENTS

Preferred embodiments of the present invention will now be described in detail in accordance with the accompanying drawings.

Exemplary embodiments of the present invention will now be described.

EMBODIMENTS

First Embodiment

In the first embodiment, an optical tomographic imaging apparatus to which the present invention is applied will be described with reference to FIG. 1A.

Figure 1A:
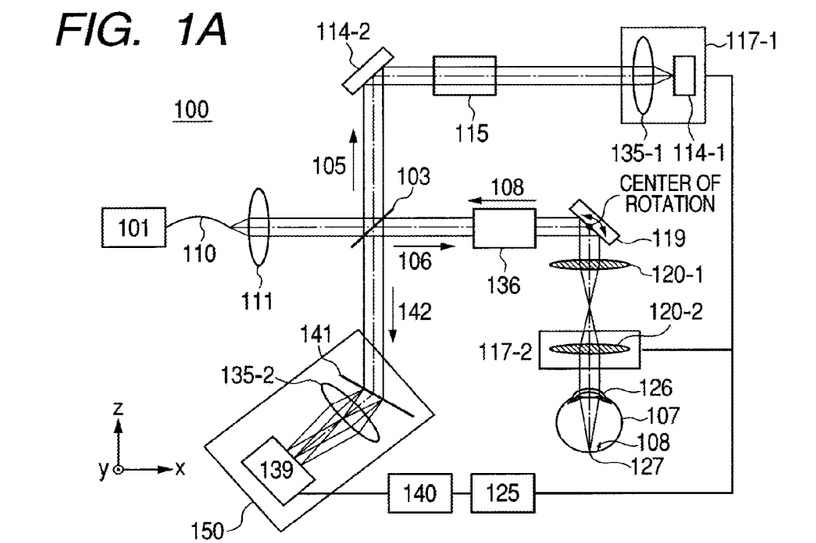

FIG. 1A illustrates an optical tomographic imaging apparatus 100, a light source 101, a beam splitter 103, a reference beam 105, a measuring beam 106, a combined beam 142, and an eye to be inspected 107 that is an object.

Also illustrated are a return beam 108, a single-mode fiber 110, lenses 111, 120 and 135, and a mirror 114.

FIG. 1A also illustrates a dispersion compensating glass 115, an electrically-powered stage 117, an X-Y-scanner 119, and a personal computer 125.

Also illustrated are a cornea 126, a retina 127, a variable beam expander 136 that is a beam diameter changing unit, a spectroscope 150 that is a detection unit, a line camera 139, a frame grabber 140, and a transmissive grating 141 that is a spectroscopic unit.

The optical tomographic imaging apparatus according to the present embodiment constitutes an OCT apparatus of Fourier domain optical coherence tomography (Fourier domain OCT).

First, a general configuration of an overall optical system of the optical tomographic imaging apparatus according to the present embodiment will be described with reference to FIG. 1A.

As illustrated in FIG. 1A, as a whole, the optical tomographic imaging apparatus 100 according to the present embodiment constitutes a Michelson interference system.

In the diagram, a light exiting the light source 101 is split into the reference beam 105 and the measuring beam 106 by the beam splitter 103. The measuring beam 106 passes through the variable beam expander 136 and is returned as a return beam 108 that is reflected or scattered by the eye to be inspected 107 that is the observation object.

After the reference beam 105 and the return beam 108 are combined by the beam splitter 103, the reference beam 105 and the return beam 108 are guided to the spectroscope 150 that constitutes a detection unit for detecting a combined beam.

The spectroscope 150 includes the transmissive grating 141 that constitutes a spectroscopic unit, a lens 135-2 that constitutes an image forming unit, and the line camera 139.

The combined beam is separated to each wavelength by the transmissive grating 141 in the spectroscope 150 and enters the line camera 139.

The line camera 139 converts light intensity into a voltage for each position (wavelength) using a line sensor that is an array of opto-electric conversion elements in the line camera 139. A tomographic image of the eye to be inspected 107 is formed using the signals. A method of forming the tomographic image will be described later.

Next, a periphery of the light source 101 will be described.

The light source 101 is an SLD (super luminescent diode) that is a typical low-coherence light source. The light source 101 has a wavelength of 840 nm and a bandwidth of 50 nm.

The bandwidth affects a resolution in an optical axis direction of a tomographic image to be obtained and is therefore an important parameter.

In addition, near-infrared light is suitable as the wavelength when considering the fact that an eye is to be measured. Furthermore, since the wavelength affects a resolution in a horizontal direction of the tomographic image to be obtained, the wavelength is desirably as short as possible. In this case, the wavelength is set to 840 nm. Depending on the object, other wavelengths may be selected.

Light output from the light source 101 passes through the single-mode fiber 110 and is guided to the lens 111, and output as collimated light.

Next, correspondence relationships between the modes and the respective beam diameters will be described.

The variable beam expander 136 constitutes a beam diameter adjustment unit and is responsible for varying a beam diameter of the measuring beam 106.

The variable beam expander 136 can vary the beam diameter by 1 to 4 mm. The beam diameter adjustment unit is not limited to the variable beam expander and a beam diameter can also be varied by selecting apertures with different diameters and inserting the apertures into an optical path of the measuring beam.

The variable beam expander is made up of a combination of a positive lens and a negative lens, not shown, whereby a beam diameter is increased (FIG. 2G) or reduced (FIG. 2E) by varying the spacing between the lenses.

In the apparatus, the beam diameter during the low-resolution mode is set to 1 mm and the beam diameter during the high-resolution mode is set to 4 mm.

Figure 2A:
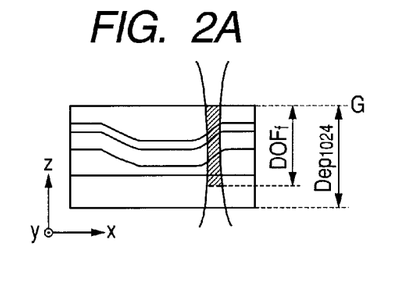
FIGS. 2A to 2D are diagrams describing relationships between gate positions and depth of focus (DOF) ranges.
Figure 2B:
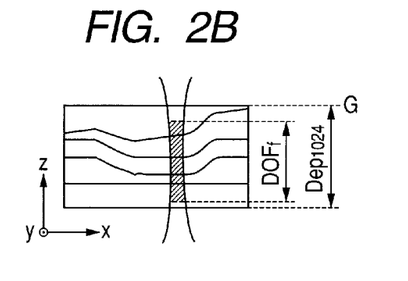
Figure 2C:
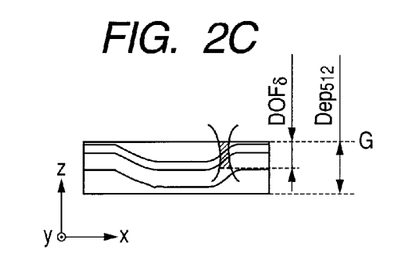
Figure 2D:
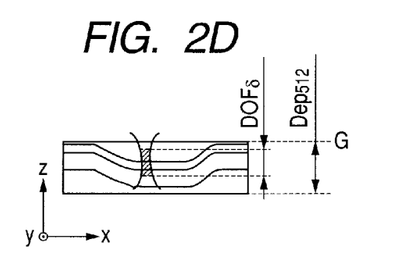
Figure 2E:
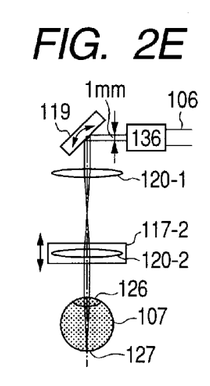
FIGS. 2E to 2H are diagrams describing a beam diameter conversion unit.
Figure 2F:
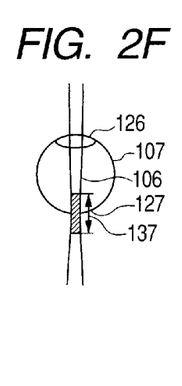

The low-resolution mode is the state illustrated in FIG. 2E where a spot diameter on the retina 127 is large.

The mode is intended to perform rough imaging of the retina over a widest possible range.

Figure 2G:
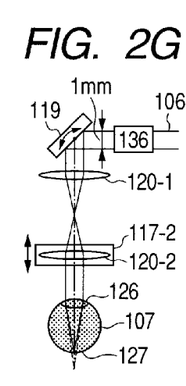
Figure 2H:
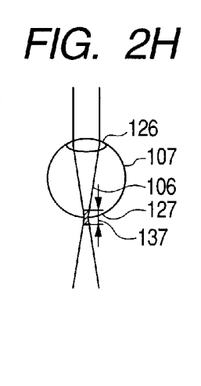

The high-resolution mode is the state illustrated in FIG. 2G where a spot diameter on the retina 127 is small. The mode is to be used when viewing a portion of interest of a retina in detail.

On the other hand, as far as the depth of focus (DOF) 137 illustrated in FIGS. 2A to 2H is concerned, the depth of focus (DOF) (to be denoted as $DOF_l$) when the beam diameter is set to 1 mm (FIG. 2E) during the low-resolution mode can be calculated using expression (2) as approximately ±1 mm (a depth of focus (DOF) range of 2 mm).

In addition, the depth of focus (DOF) (to be denoted as $DOF_h$) when the beam diameter is set to 4 mm (FIG. 2G) can be calculated as approximately ±0.05 mm (a depth of focus (DOF) range of 0.1 mm).

Furthermore, using expression (1), horizontal resolutions Rxy can be respectively calculated as approximately 20 μm when the beam diameter is set to 1 mm (FIG. 2E) and as approximately 5 μm when the beam diameter is set to 4 mm (FIG. 2G). Therefore, a high-definition tomographic image with high horizontal resolution can be obtained in the high-resolution mode.

$$Rxy=k_1 \cdot \lambda/NA \qquad \text{Expression (1),}$$

where $k_1$ is a constant around 0.5.

On the other hand, the depth of focus (DOF) of the imaging system can be expressed by $$DOF=\pm k_2 \cdot (\lambda/NA^2) \qquad \text{Expression (2),}$$

where $k_2$ is a constant around 0.6.

In the above expressions, DOF denotes a depth of focus (DOF), Rxy a horizontal resolution, NA a numerical aperture in an eye that forms an image of a collimated measuring beam, and λ a central wavelength of the measuring beam.

NA is determined by a beam diameter and a focal length of the eye, and if the focal length of the eye is set to 22.5 mm, then NA≈d/(2·f), where d denotes a beam diameter and f denotes the focal length of the eye at the time of measurement.

In the above calculations, $NA_{d=1mm}=0.022$ when the beam diameter is set to 1 mm and $NA_{d=4mm}=0.088$ when the beam diameter is set to 4 mm have been used.

Next, an optical path of the reference beam 105 will be described.

The reference beam 105 split by the beam splitter 103 is incident to a mirror 114-2 to change direction, condensed by a lens 135-1 at a reference mirror 114-1, and is then reflected and redirected to the beam splitter 103.

Next, the reference beam 105 passes through the beam splitter 103 and is guided to the spectroscope 150.

The dispersion compensating glass 115 compensates, with respect to the reference beam 105, dispersion that occurs when the measuring beam 106 travels to and from the eye to be inspected 107 or, in other words, dispersions of an optical system used for forming an image on an eyeball that is a measured object.

In addition, an electrically-powered stage 117-1 constitutes a control unit for controlling the position of the reference mirror. Accordingly, an optical path length of the reference beam 105 from start to end of imaging can be adjusted and controlled.

Furthermore, the electrically-powered stage 117-1 can be controlled by the personal computer 125.

Next, an optical path of the measuring beam 106 will be described.

The measuring beam 106 split by the beam splitter 103 is incident to a mirror of the X-Y-scanner 119.

While the X-Y-scanner 119 is described as a single mirror for simplicity, in reality, two mirrors, namely, an X-scanning mirror and a Y-scanning mirror are arranged in close proximity of each other to perform a raster-scan on the retina 127 in a direction perpendicular to the optical axis. In addition, the center of the measuring beam 106 is arranged to be consistent with a center of rotation of the mirror of the X-Y-scanner 119.

Lenses 120-1 and 120-2 are an optical system that constitutes a condensing unit that condenses the measuring beam at an object for scanning the retina 127 that is the object.

As illustrated in FIG. 1A, the X-Y-scanner 119 and the optical system are responsible for scanning the retina 127 with the measuring beam 106 while setting a pivot point in a vicinity of the cornea 126.

In this case, the focal lengths of the lenses 120-1 and 120-2 are respectively set to 50 mm.

Moreover, an electrically-powered stage 117-2 constitutes a control unit for controlling the position of the condensing unit and is capable of adjusting and controlling the position of an ancillary lens 120-2.

By adjusting the position of the lens 120-2, the measuring beam 106 can be condensed at a desired layer of the retina 127 of the eye to be inspected 107 that is an object from the start to end of imaging, and observation can be performed.

A case where the eye to be inspected 107 contains a refractive error can also be accommodated.

After entering the eye to be inspected 107, the measuring beam 106 becomes the return beam 108 due to reflection or scattering from the retina 127. The return beam 108 is reflected by the beam splitter 103 and guided to the line camera 139.

The electrically-powered stage 117-2 can also be controlled by the personal computer 125.

Next, a configuration of a measurement system of the OCT apparatus according to the present embodiment will be described.

The return beam 108 that is light reflected or scattered off of the retina 127 is reflected by the beam splitter 103.

The reference beam 105 and the return beam 108 are adjusted so as to be combined behind the beam splitter 103.

The combined beam 142 is separated into each wavelength by the transmissive grating 141, condensed by the lens 135-2, and light intensity is converted into voltage by the line camera 139 for each position (wavelength).

Specifically, interference fringes of a spectrum region on a wavelength axis are to be observed on the line camera 139.

The OCT apparatus is designed and adjusted such that a 50 nm separated beam with which the lens 135-2 forms an image on the line sensor that is an array of opto-electric conversion elements approximately corresponds to the number of pixels of the line sensor to read out by the line camera.

The line sensor is configured to temporally sequentially read out signals obtained by the opto-electric conversion elements aligned in a single row.

However, in the present embodiment, the line sensor is provided with two registers, wherein odd-number pixels are connected to one register and even-number pixels are connected to the other register.

On the other hand, the 50 nm separated beam forms an image on a width corresponding to 1024 pixels of a sensor inside the line camera 139.

Figure 1B:
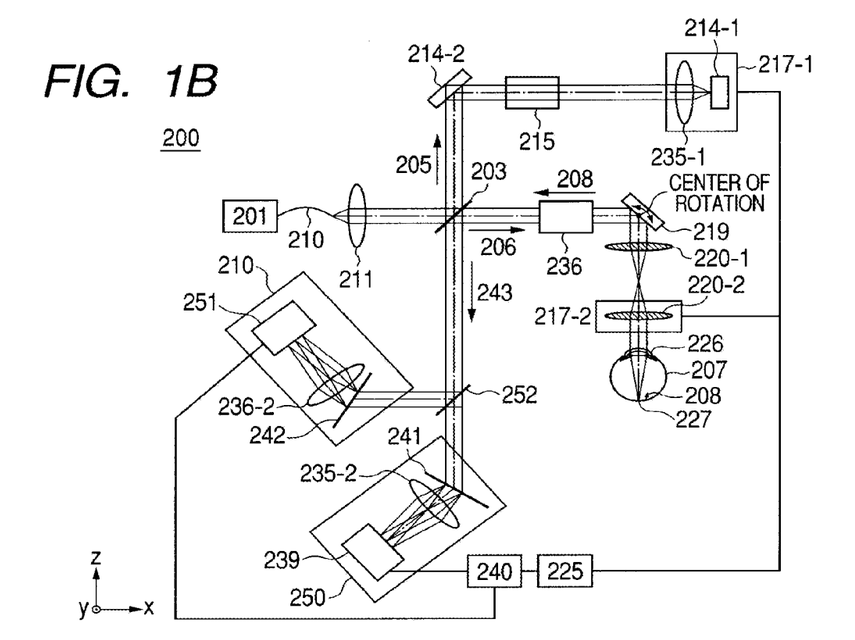

FIG. 1B schematically illustrates a line sensor 139-1. Separated beams ranging from λs (815 nm) to λe (865 nm) form an image on the line sensor 139-1.

A group of obtained voltage signals is converted into digital values by the frame grabber 140 and subjected to data processing by the personal computer 125 to form a tomographic image.

In this case, the line camera 139 has 1024 pixels as described earlier and can obtain an intensity of the combined beam 142 for each wavelength.

A method of obtaining a tomographic image using the present apparatus will now be described.

A method of acquiring a tomographic image (surface parallel to the optical axis) of the retina 127 will be described using FIGS. 1A and 2A to 2D.

After passing through the cornea 126 and entering the retina 127, the measuring beam 106 becomes the return beam 108 due to reflection and scattering at various positions and reaches the line camera 139.

Figure 3A:
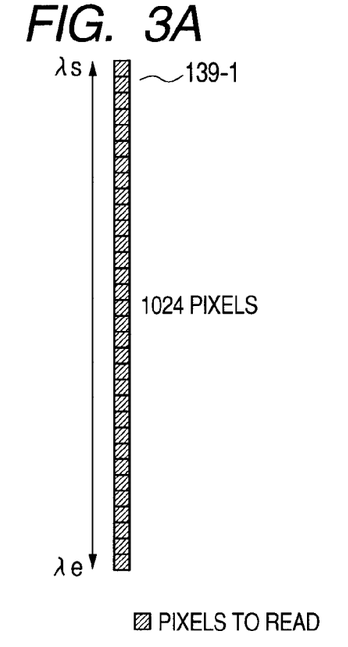
FIGS. 3A, 3B, 3C and 3D are diagrams describing operations of line sensors according to the first and second embodiments of the present invention.
Figure 3B:
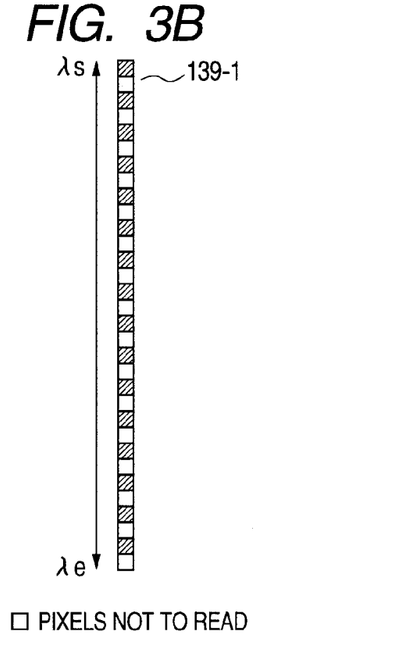

Since the bandwidth of the light source 101 has a wide bandwidth and a short spatial coherence length, when the optical path length of the reference light path and the optical path length of the measurement light path are approximately equal, interference fringes can be detected by the line sensor 139-1 (refer to FIGS. 3A and 3B).

As described earlier, interference fringes acquired by the line sensor 139-1 correspond to a spectrum region on the wavelength axis.

Next, in consideration of the characteristics of the line sensor 139-1 and the transmissive grating 141, the interference fringes that are information on the wavelength axis are converted into interference fringes on an optical frequency axis.

Furthermore, information in a depth direction can be obtained by performing inverse Fourier transform on the converted interference fringes on the optical frequency axis.

Moreover, an interference fringe can be obtained for each X-axis position by detecting the interference fringes while driving the X-axis of the X-Y-scanner 119.

In other words, information in the depth direction of each X-axis position can be obtained.

One-dimensional data of a position in an X-direction with respect to a depth direction (Z-direction in an XYZ coordinate) will be referred to as an A-scan.

By sequentially arranging A-scans of all X positions to be subjected to imaging in a time series in which the X-scanner is rotated, a two-dimensional distribution of intensities of the return beam 108 on the XZ plane and tomographic images shown in FIGS. 2A to 2D are obtained. The resulting data will be referred to as a B-scan.

Spot diameters at a measured object differ between the low-resolution mode and the high-resolution mode described above. In particular, in the high-resolution mode, respective X-axis positions must be obtained at fine intervals so as to take advantage of the horizontal resolution of the high-resolution mode for B-scans. As such, a B-scan is combined after obtaining A-scans at intervals of around 5 μm that is the resolution of the high-resolution mode.

In addition, in the low-resolution mode, A-scans are to be obtained at intervals of around 20 μm that is the resolution of the low-resolution mode.

As described earlier, a tomographic image is an array-like arrangement of obtained B-scan intensities and is displayed by, for example, extrapolating the intensities to a grayscale. In the display, only boundaries of the obtained tomographic image have been highlighted.

Next, relationships between a measurement distance from a gate, the number of pixels, and a depth of focus (DOF) will be described.

Now, in FIGS. 2A to 2D, a position of an optical path length that is the same as the reference mirror 114-1 on the measuring beam-side will be denoted as a gate position G and an optical distance from G on which imaging can be performed by the present apparatus will be denoted as an imaging optical distance Dep.

Interference fringes become finer as the optical distance of the portion to be subjected to imaging becomes longer.

In consideration of a limit to which finer interference fringes can be detected, the imaging optical distance Dep is determined by a separated wavelength width and the number of pixels corresponding to a wavelength width to be received by the line sensor 139-1.

$$Dep = N/(4 \cdot \Delta K) \quad \text{Expression (3)},$$

where Dep denotes an imaging optical distance, $\Delta K$ denotes a wave number expression of a wavelength width of a light source used for measurement, and N denotes the number of pixels in a region in which an image is formed by a bandwidth of a wavelength included in a combined beam.

If $\lambda_s$ denotes a wavelength with the shortest wavelength bandwidth and $\lambda_e$ a wavelength with the longest wavelength bandwidth, then $\Delta K$ may be calculated using expression (4). By substituting $\lambda_s = 815$ nm, $\lambda_e = 865$ nm of the present embodiment, then $\Delta K = 7.1 \times 10^{-5}$ (1/nm).

$$\Delta K = |1/\lambda_s - 1/\lambda_e| \quad \text{Expression (4)}$$

By substituting the value of $\Delta K$ into expression (3), then $Dep_{1024} = 3.6$ mm for 1024 read pixels and $Dep_{512} = 1.8$ mm for 512 read pixels.

Meanwhile, with an OCT apparatus for Fourier domain optical coherence tomography, the relationship between a gate position G in FIGS. 2A to 2D and a measured object typically involves separating the gate position G from a surface of the measured object. This is because a fundamental problem exists in that when the gate position G is moved inside of the measured object, a mirror image obtained by Fourier transform overlaps a real image.

In addition, when a focusing position of the measured object is adjusted to place as much of the measured object within the depth of focus (DOF) range as possible, imaging of a widest range can be favorably performed with respect to the depth direction of the measured object.

Next, a relationship between a gate position, a depth of focus (DOF) range, and an imaging optical distance for each mode will be described.

First, the low-resolution mode will be described with reference to FIGS. 2A and 2B. As described earlier, the beam diameter is set to 1 mm and the depth of focus (DOF) range is set to 2 mm.

As illustrated in FIG. 1A, the reference mirror 114-1 is moved by the electrically-powered stage 117-1 with respect to the measured object.

Let us assume that from a gate position G adjusted as described above, the lens 120-2 is moved in the Z-direction by the electrically-powered stage 117-2 so as to enter the depth of focus (DOF) range to adjust a focusing position.

If there are 1024 read pixels, then imaging optical distance $Dep_{1024} = 3.6$ mm>depth of focus $DOF_1 = 2$ mm, signifying that imaging can be performed on the information on the measured object in the depth of focus (DOF) in this mode. In addition, as illustrated in FIG. 2B, when there are irregularities on the measured object and the gate position G is to be separated from the surface of the measured object, an attention portion is to be adjusted so as to be included in the depth of focus (DOF).

Accordingly, imaging can be performed without being affected by a mirror image within a condition of imaging optical distance $Dep_{1024} = 3.5$ mm (depth of focus (DOF)+ distance from gate position to measured object surface).

Next, the high-resolution mode will be described with reference to FIGS. 2C and 2D.

The beam diameter is set to 4 mm and the depth of focus (DOF) is set to 0.1 mm. Let us assume that the gate position G has been approximately aligned with the measured object surface and the focusing position is adjusted to bring a range of 0.1 mm from the measured object surface into the depth.

When a structure of the measured object to be obtained at high resolution is only present in a vicinity of the depth of focus (DOF) or, in other words, when information deep in the Z-direction need not be obtained, then there is no need to read all pixels of the line sensor.

In such a case, the line sensor is read by thinning every other pixel as illustrated in FIG. 3B. Accordingly, reading time can be reduced.

In other words, an acquisition time of one A-scan is reduced.

When a line sensor is thinned and read and the number of pixels is thinned out to 512 read pixels, then imaging optical distance $Dep_{512} = 1.8$ mm>depth of focus (DOF)=0.1 mm, signifying that imaging can be performed on the information on the measured object in the depth of focus (DOF) in this mode.

In addition, in the same manner as in the low-resolution mode described earlier, for example, when there are irregularities on the measured object and the gate position G is to be separated from the surface of the measured object, imaging can be performed without being affected by a mirror image within a condition of imaging optical distance $Dep_{512} = 1.8$ mm≥(depth of focus (DOF)+distance from gate position to measured object surface).

Configurations of the line sensor 139-1 when thinning is to be performed include a configuration in which, as described earlier, two registers are prepared and aligned pixels are alternately connected, whereby reading is performed from only one register (for example, the register to which odd-number pixels are connected) during thinning.

Since the high-resolution mode is capable of reducing the number of pixels to read for an A-scan, the imaging time of a measured object when obtaining and combining a large number of A-scans in the A-scan high-resolution mode can be reduced as compared to reading out all 1024 pixels.

In order to acquire A-scans at even faster speeds, reading can be performed by thinning two consecutive or three consecutive pixels to read.

In doing so, the number of pixels may be a number satisfying an imaging optical distance Dep determined from a relationship between a depth of focus (DOF) determined by a beam diameter and a depth of an attention site.

For instance, in the example described above, since the depth is 0.1 mm for a beam diameter of 4 mm, when imaging is to be performed to a depth of 0.1 mm from a gate position, thinning three consecutive pixels results in 256 pixels to read for the imaging optical distance Dep.

Since an imaging optical distance $Dep_{256}$ for 256 pixels can be calculated as 0.9 mm from expression (3), measurements can be sufficiently performed with only 256 pixels depending on a gate position and on how a depth of focus (DOF) range is to be adjusted.

As shown, since the optical tomographic imaging apparatus according to the present embodiment is provided with a low-resolution mode and a high-resolution mode and a focusing range is reduced in the high-resolution mode, a depth-direction range to be subjected to imaging can be narrowed down depending on the object and the number of pixels to read can be reduced.

Since the time required for acquiring an A-scan can be reduced, higher speeds can be realized as compared to reading out all pixels.

In addition, the optical tomographic imaging apparatus according to the present embodiment is effective for constructing a B-scan since the number of pixels making up a single A-scan that forms a basis of the B-scan is reduced and processing speed can be increased.

The present embodiment is not intended to limit a beam diameter and, for example, the low-resolution mode may be readily modified so that the beam diameter is set to 2 mm and the high-resolution mode may be readily modified so that the beam diameter is set to 6 mm.

Second Embodiment

Next, an optical tomographic imaging apparatus for Fourier domain optical coherence tomography according to a second embodiment will be described with reference to FIG. 1B.

Unlike the first embodiment, the present embodiment includes a plurality of detection units, wherein each of the detection units has a spectroscope with a different configuration.

Otherwise, the configuration as an apparatus is similar to the first embodiment. Accordingly, descriptions of overlapping portions will be omitted.

First, a general configuration of an overall optical system of the optical tomographic imaging apparatus according to the present embodiment will be described.

FIG. 1B illustrates an optical tomographic imaging apparatus 200, a light source 201, beam splitters 203 and 252, a reference beam 205, a measuring beam 206, a combined beam (interference light) 243, an eye to be inspected 207, a return beam 208, and a single-mode fiber 210.

Also illustrated are lenses 211, 220, 235, and 236, a mirror 214, a dispersion compensating glass 215, an electrically-powered stage 217, an X-Y-scanner 219, and a personal computer 225.

FIG. 1B also illustrates a cornea 226, a retina 227, a variable beam expander 236 that is a beam diameter changing unit, spectroscopes 250 and 251, line cameras 238 and 239, a frame grabber 240, and transmissive gratings 241 and 242.

The OCT apparatus 200 according to the present embodiment is the same as in the first embodiment until the interference light 243 is combined.

The interference light 243 is split by the beam splitter 252, whereby a portion of the split light is guided to the spectroscope 250 and another portion is guided to the spectroscope 251. Overall operations of each spectroscope are similar to the first embodiment.

A light source similar to the first embodiment is used. The SLD has a wavelength of 840 nm and a bandwidth of 50 nm.

In addition, the variable beam expander 236 is responsible for varying a beam diameter of the measuring beam 206.

The variable beam expander 236 can vary the beam diameter by 1 to 4 mm.

Similarly in the present embodiment, the beam diameter is set to 1 mm in the low-resolution mode and to 4 mm in the high-resolution mode.

Therefore, values of respective depths of focus (DOF) and resolutions are the same as in the first embodiment.

Furthermore, optical paths of the measuring beam and the reference beam are also the same as in the first embodiment.

Next, a configuration of a measurement system in the OCT apparatus according to the present embodiment will be described.

The combined beam 243 is split by the beam splitter 252 and respectively guided to the spectroscopes 250 and 251.

In this case, the spectroscope 250 is a spectroscope for the low-resolution mode and the spectroscope 251 is a spectroscope for the high-resolution mode.

Beams incident to the respective spectroscopes 250 and 251 are separated into each wavelength by the transmissive gratings 241 and 242, condensed by lenses 235-2 and 236-2, and light intensity is converted into voltage by the line cameras 238 and 239 for each position (wavelength).

In doing so, the line camera 238 is driven in the low-resolution mode and the line camera 239 is driven in the high-resolution mode.

Specifically, interference fringes of a spectrum region on a wavelength axis are to be observed on the line cameras 238 and 239.

The OCT apparatus is designed and adjusted such that a 50 nm separated beam with which the lenses 235-2 and 236-2 form an image on the line sensors inside the line cameras 238 and 239 approximately corresponds to the number of pixels of the line sensors to be read out by the line cameras.

Unlike the first embodiment, each line sensor is provided with only one register.

Specifically, at the spectroscope 250, the bandwidth of the 50 nm separated beam forms an image on a width corresponding to 1024 pixels of a sensor inside the line camera 238.

Figure 3C:
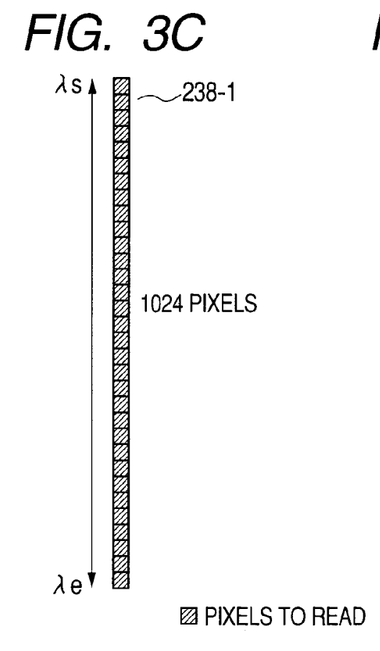

FIG. 3C schematically illustrates a line sensor 238-1. Separated beams ranging from $\lambda_s$ (815 nm) to $\lambda_e$ (865 nm) form an image on the line sensor 238-1. In addition, at the spectroscope 251, the bandwidth of the 50 nm separated beam forms an image on a width corresponding to 512 pixels of a sensor inside the line camera 239.

Figure 3D:
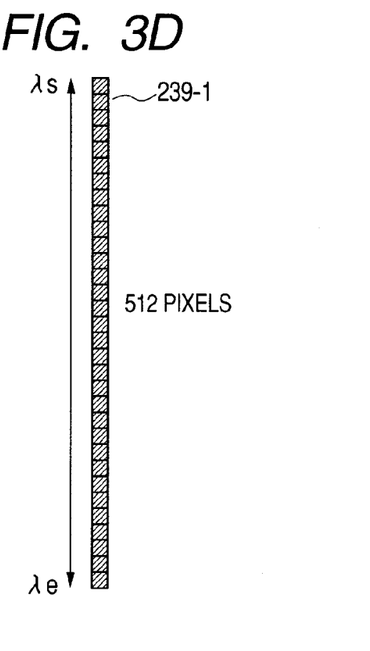

FIG. 3D schematically illustrates a line sensor 239-1. Separated beams ranging from $\lambda_s$ (815 nm) to $\lambda_e$ (865 nm) form an image on the line sensor 239-1. Each spectroscope may vary a ratio between bandwidth and the number of line sensor pixels by varying any of a lens focal length, a transmissive grating pitch, and a width of a single pixel of the line sensor itself, or varying a combination thereof.

The frame grabber 240 converts a group of voltage signals obtained from the line camera 238 in the low-resolution mode and from the line camera 239 in the high-resolution mode into digital values, and performs data processing at the personal computer 225 to form a tomographic image.

In this case, the line camera 239 can obtain an intensity of the combined beam 243 for each wavelength.

Since the method of acquiring a tomographic image is the same as the first embodiment, a description will be omitted. An imaging optical distance for each mode is also the same as the first embodiment.

As for a relationship between gate distance and depth of focus (DOF), operations in the low-resolution mode are the same as in the first embodiment and a description will be omitted.

Next, the high-resolution mode according to the present embodiment will be described.

A basic positional relationship between a gate position and a depth of focus (DOF) range is the same as in the first embodiment.

The beam diameter is set to 4 mm and the depth of focus (DOF) is set to 0.1 mm. Let us assume that the gate position G has been approximately aligned with the measured object surface and the focusing position is adjusted to bring a range of 0.1 mm from the measured object surface into the depth.

Since the line sensor 239-1 of the spectroscope 251 selected in the high-resolution mode has 512 pixels, imaging optical distance $Dep_{512}$=1.8 mm>depth of focus (DOF)=0.1 mm, which signifies that imaging can be performed on the information on the measured object in the depth of focus (DOF) in this mode.

In addition, in the same manner as the low-resolution mode described earlier, for example, when there are irregularities on the measured object and the gate position G is to be separated from the surface of the measured object, imaging can be performed without being affected by a mirror image within a condition of imaging optical distance $\text{Dep}_{512}=1.8$ mm≥(depth of focus (DOF)+distance from gate position to measured object surface).

Since the high-resolution mode is capable of reducing the number of pixels to read for an A-scan, the imaging time of a measured object when obtaining and combining a large number of A-scans in the A-scan high-resolution mode can be reduced as compared to reading out all pixels.

As shown, the optical tomographic imaging apparatus according to the present embodiment is provided with a low-resolution mode and a high-resolution mode, and a spectroscope provided with a line sensor having a fewer number of pixels to read can be selected in the high-resolution mode.

When the spectroscope is selected, since the time required to acquire an A-scan can be reduced due to a reduction in sensor read time, higher speeds can be achieved.

The present embodiment is not intended to limit a beam diameter and, in the same manner as in the first embodiment, for example, the low-resolution mode may be modified so that the beam diameter is set to 2 mm and the high-resolution mode may be modified so that the beam diameter is set to 6 mm.

Third Embodiment

Next, an optical tomographic imaging apparatus for Fourier domain optical coherence tomography according to a third embodiment will be described with reference to FIGS. 4A to 4E.

Compared to the first embodiment, the present embodiment adopts a zone focusing method in which, in a high-resolution mode, focus positions are changed in stages and a plurality of B-scan images obtained at respective positions is pieced together.

Accordingly, a configuration can be realized in which a tomographic image acquired during a narrow depth of focus (DOF) in the high-resolution mode can be obtained to a deeper position.

Otherwise, the configuration as an apparatus is similar to the first embodiment. As such, descriptions of overlapping portions will be omitted.

First, a general configuration of an overall optical system of the optical tomographic imaging apparatus according to the present embodiment will be described.

Figure 4A:
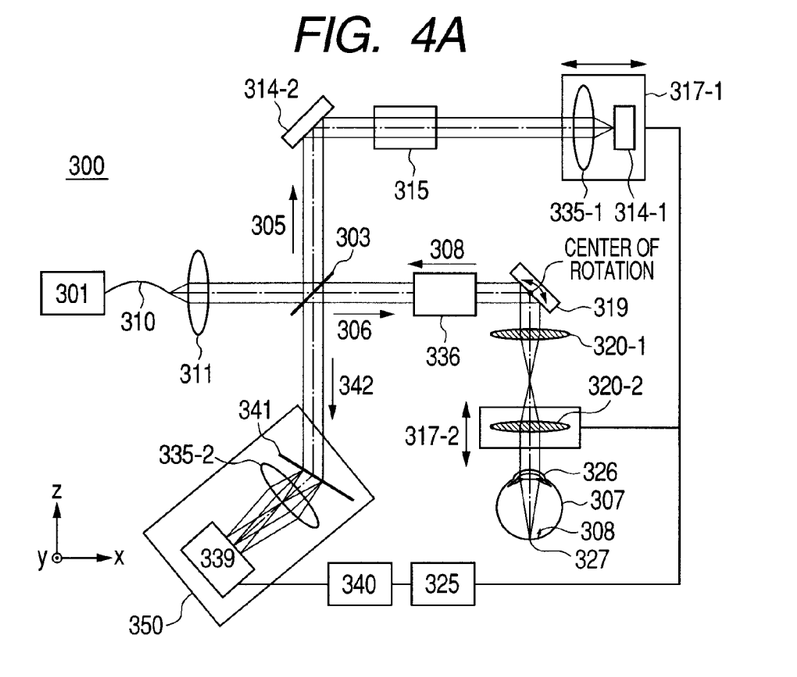
FIG. 4A is a diagram describing a configuration of an optical system of an optical tomographic imaging apparatus.

FIG. 4A illustrates an optical tomographic imaging apparatus 300, a light source 301, a beam splitter 303, a reference beam 305, a measuring beam 306, a combined beam 342, an eye to be inspected 307, a return beam 308, and a single-mode fiber 310.

Also illustrated are lenses 311, 320 and 335, a mirror 314, a dispersion compensating glass 315, an electrically-powered stage 317, an X-Y-scanner 319, and a personal computer 325.

FIG. 4A also illustrates a cornea 326, a retina 327, a variable beam expander 336 that is a beam diameter changing unit, a spectroscope 350, a line camera 339, a frame grabber 340, and a transmissive grating 341.

Operations of the optical tomographic imaging apparatus 300 according to the present embodiment in a low-resolution mode are the same as in the first embodiment.

During an imaging operation in the high-resolution mode, a lens 320-2 is moved by minute step amounts by an electrically-powered stage 317-2 that is a control unit for controlling the positions of the lens 320-2 that constitutes a condensing unit.

In association with the step movement of the lens 320-2, a reference mirror 314-1 is also moved in minute steps by an electrically-powered stage 317-1 that is a control unit for controlling the position of the reference mirror. Movement amounts of the lens 320-2 and the reference mirror 314-1 will be described later.

A light source similar to the first embodiment is used. The SLD has a wavelength of 840 nm and a bandwidth of 50 nm.

In addition, the variable beam expander 336 is responsible for varying a beam diameter of the measuring beam 306. The variable beam expander 236 can vary the beam diameter by 1 to 4 mm.

In the present embodiment, the beam diameter is set to 1 mm in the low-resolution mode and to 2 mm in the high-resolution mode.

Therefore, values of a depth of focus (DOF) and a resolution in the low-resolution mode are the same as in the first embodiment. A depth of focus (DOF) in the high-resolution mode, $\text{NA}_{d=2mm}$, can be calculated from $\text{NA}=d/(2\cdot f)$ as 0.044, and as approximately ±0.3 mm (a depth of focus (DOF) range of 0.6 mm) using expression (2). In addition, a resolution $\text{Rxy}_{d=2mm}$ can be calculated as approximately 10 μm.

Furthermore, optical paths of the measuring beam and the reference beam are also the same as in the first embodiment.

A configuration of a measurement system is the same as in the first embodiment. Thinning and reading of pixels at a line sensor 339-1 of the line camera 339 in the high-resolution mode are similarly performed.

Therefore, a configuration of the register in the line sensor is also the same as the first embodiment.

A relationship between a zone focusing operation in the high-resolution mode and an imaging optical distance $\text{Dep}_{512}$ will now be described with reference to FIGS. 4B to 4D.

In the high-resolution mode, zone focusing is operated in four stages to load B-scan images, followed by image composition that involves piecing the images together.

Figure 4B:
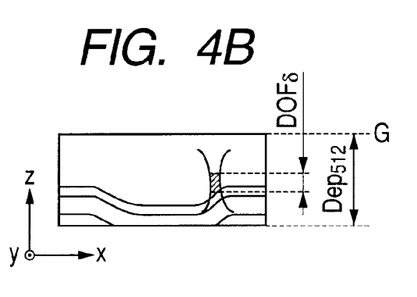
FIGS. 4B to 4E are diagrams describing relationships between gate positions and depth of focus (DOF) ranges during zone focusing.
Figure 4C:
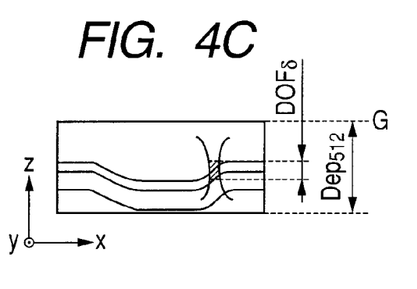
Figure 4D:
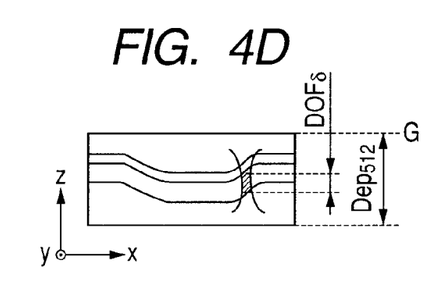
Figure 4E:
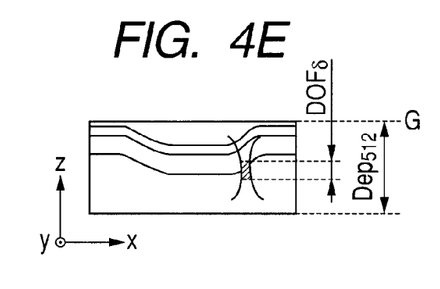

FIGS. 4B to 4D illustrate a gate position G and a depth of focus (DOF) range $\text{DOF}_h$ of each stage of zone focusing.

FIG. 4B illustrates a state of a first state of zone focusing where the lens 320-2 is to be adjusted so that $\text{DOF}_h$ is positioned near the surface of the retina that is a measured object.

Meanwhile, the mirror 314-1 is to be moved and adjusted so that the gate position G is situated above the $\text{DOF}_h$.

An ordinary B-scan image is acquired at this position and stored in a memory, not shown, in the personal computer 325.

In a next zone focusing state, as illustrated in FIG. 4C, the depth of focus (DOF) range $\text{DOF}_h$ and the gate position G are moved simultaneously.

In doing so, the depth of focus (DOF) range $\text{DOF}_h$ is moved 0.5 mm, which is 0.1 mm shorter than the length 0.6 mm of $\text{DOF}_h$, in the Z-direction by the movement of the lens 320-2 caused by the electrically-powered stage 317-2.

The gate position is moved accordingly by moving the reference mirror 314-1 0.5 mm by the electrically-powered stage 317-1. A B-scan is acquired in this state.

Travel distance is set shorter than the depth of focus (DOF) range in order to improve accuracy when piecing together acquired images by using high-resolution images in the depth of focus (DOF) as images in an overlapping portion.

In a next zone focusing state, similarly, the depth of focus (DOF) range $\text{DOF}_h$ and the gate position G are respectively moved 0.5 mm to acquire a B-scan.

From the four B-scan images, a total depth of focus (DOF) range due to the four-stage movement is 2 mm.

The four B-scan images are pieced together according to the travel distance of zone focusing on the personal computer 325 to obtain an image with a wide Z-directional range at a high horizontal resolution.

Moving the gate position G in association with the adjustment of the depth of focus (DOF) range is essential because the Z-directional length of 2 mm of the image to be obtained by zone focusing is greater than the imaging optical distance $Dep_{512}=1.8$ mm for reading 512 pixels.

In addition, characteristically in Fourier domain OCT, the further away from the gate position, the lower the obtained signal intensity.

When the distance from the gate position G to the depth of focus (DOF) range is the same when acquiring a B-scan in each zone focusing stage, an advantage is gained in terms of signal intensity rather than in terms of a condition for fixing gate positions.

In this case, by reducing the number of pixels to 512 in the high-resolution mode, in addition to a higher reading speed in comparison to reading 1024 pixels in the same manner as in the first embodiment, a higher processing speed can also be achieved.

In other words, a higher processing speed is achieved because B-scan images corresponding to one zone focusing stage when piecing together B-scans obtained through zone focusing are smaller.

As described above, the optical tomographic imaging apparatus according to the present embodiment is provided with a low-resolution mode and a high-resolution mode, and uses a zone focusing method in the high-resolution mode.

Consequently, pixels to read during zone focusing can be reduced, enabling a reduction in the time required to acquire an A-scan which, in turn, enables a reduction in the time required to acquire a B-scan.

Furthermore, a higher processing speed is achieved because B-scan images corresponding to one zone focusing stage when piecing together B-scans obtained through zone focusing are smaller. Moreover, the present embodiment is not intended to limit a beam diameter and in the same manner as in the first embodiment, for example, the low-resolution mode may be modified so that the beam diameter is set to 2 mm and the high-resolution mode may be modified so that the beam diameter is set to 4 mm.

Fourth Embodiment

Next, an optical tomographic imaging apparatus for Fourier domain optical coherence tomography according to a fourth embodiment will be described with reference to FIGS. 5A and 5B.

The present embodiment differs from the third embodiment in how a spectroscope is configured, and is arranged so that a wavelength width per pixel of an opto-electric conversion element array is varied by the zooming lens to form an image on the opto-electric conversion element array.

The tomographic image is arranged to be formed from data of pixels in a range of the formed image.

Otherwise, the configuration as an apparatus is similar to the third embodiment. Accordingly, descriptions of overlapping portions will be omitted.

FIGS. 5A to 5D illustrate a spectroscope 450, a transmissive grating 441, and lenses 435-2 and 435-3. The two lenses are combined to form a zooming lens.

FIGS. 5A to 5D also illustrate a line camera 439.

Operations of the optical tomographic imaging apparatus in a low-resolution mode and in a high-resolution mode are the same with the exception of a portion of the spectroscope.

In other words, adjustment of a depth of focus (DOF) range, adjustment of a gate position, a procedure of zone focusing for acquiring a B-scan by varying a position of the depth of focus (DOF) range in stages, and the like in the high-resolution mode are also the same.

A light source similar to the first embodiment is used. The SLD has a wavelength of 840 nm and a bandwidth of 50 nm.

Using a variable expander, the beam diameter is set to 1 mm in the low-resolution mode and to 2 mm in the high-resolution mode.

Therefore, values of a depth of focus (DOF) and a resolution of each mode are the same as in the third embodiment. Furthermore, optical paths of the measuring beam and the reference beam are also the same as in the first embodiment.

Operations around the spectroscope will now be described with reference to FIGS. 5A, 5B, 6A and 6B.

First, the state of the spectroscope in the low-resolution mode will be described.

In the same manner as in the first to third embodiments, a combined beam is guided to the spectroscope 450.

Figure 5A:
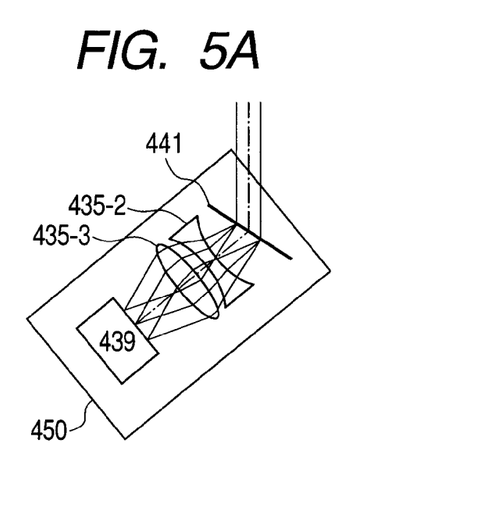
FIGS. 5A, 5B, 5C and 5D are diagrams describing spectroscopes of optical tomographic imaging apparatuses according to the fourth and fifth embodiments of the present invention.

In the low-resolution mode, as illustrated in FIG. 5A, the lenses 435-2 and 435-3 are adjusted as a zooming lens to a long-focus state.

A combined beam separated into each wavelength by the transmissive grating 441 is condensed by the lenses 435-2 and 435-3.

The respective lenses 435-2 and 435-3 are adjusted as a zooming lens so that an image is formed on a line sensor 439-1 in the line camera 439 and a 50 nm bandwidth separated beam corresponds to the number of pixels in the line sensor.

Figure 6A:
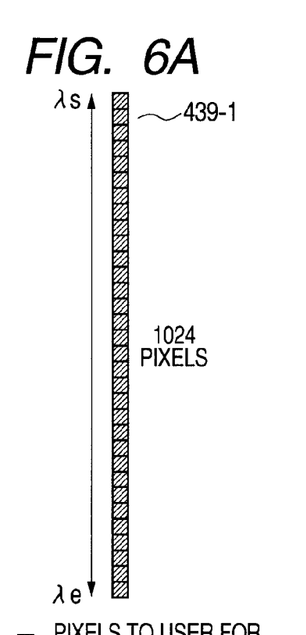

Specifically, as illustrated in FIG. 6A, the 50 nm separated beam forms an image on a width corresponding to 1024 pixels of a sensor inside the line camera 439.

FIG. 6A schematically illustrates the line sensor 439-1. Separated beams ranging from $\lambda_s$ (815 nm) to $\lambda_e$ (865 nm) form an image on the line sensor 439-1. This spectroscope state is similar to the third embodiment.

Next, the state of the spectroscope in the high-resolution mode will be described.

Figure 5B:
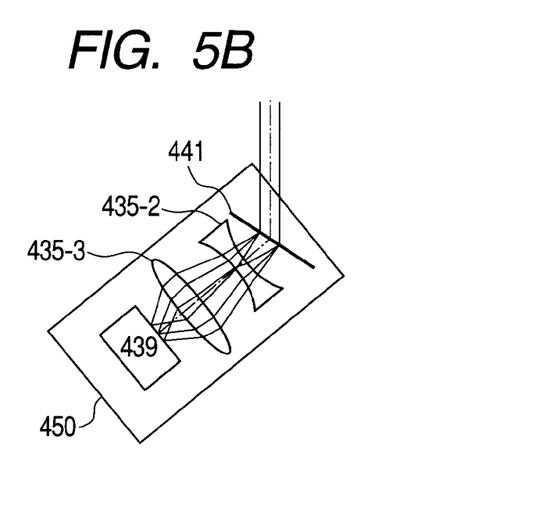

In the high-resolution mode, as illustrated in FIG. 5B, the lenses 435-2 and 435-3 are adjusted as a zooming lens to a short-focus state.

Figure 6B:
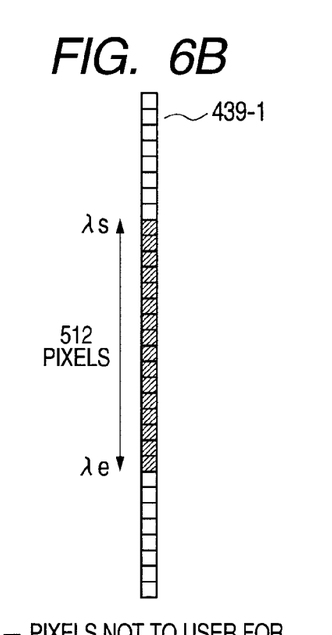

Accordingly, light separated into each wavelength by the transmissive grating 441 or, in other words, a 50 nm bandwidth light forms an image across a width corresponding to 512 pixels as illustrated in FIG. 6B.

While data corresponding to 1024 pixels is read during reading, data corresponding to 512 pixels is used when performing processing such as FFT for structuring a B-scan image at each depth of focus (DOF) position and when piecing together the respective B-scans. In other words, only data of pixels corresponding to an image formed by the combined beam on the opto-electric conversion element array is used.

Accordingly, the time required for structuring an image in the high-resolution mode can be reduced. At the same time, since less loss of the light quantity of the combined beam occurs in comparison to the thinning and reading of the line sensor in the third embodiment, the contrast of an obtained image is increased.

Furthermore, the opto-electric conversion element array may be subjected to region splitting and arranged so that data of pixels in at least one split region can be read independently from other split regions.

Specifically, for example, by providing the line sensor 439-1 in advance with a register so that reading from 512 pixels in a central portion can be performed independently, only the 512 pixels of the central portion of the line sensor 439-1 can be arranged so as to be read in the high-resolution mode.

In doing so, in addition to speeding up image formulation, there is no need to read out data corresponding to 1024 pixels.

Therefore, the read time of the line sensor can be reduced and a further reduction in imaging time can be achieved.

As described above, in the present embodiment, the absence of light quantity loss during imaging in the high-resolution mode using zone focusing results in a higher image contrast and a shorter imaging time.

The present embodiment is not intended to limit an image-forming range by the zooming lens to 1024 or 512 pixels and, for example, 256 pixels and the like can be freely selected.

In addition, while it is conceivable that an image formation position becomes offset due to a zooming operation of a lens with respect to the line sensor, in such a case, a mechanism may be provided for automatically or manually adjusting a positional relationship between the line sensor and the lens depending on the mode.

Fifth Embodiment

Next, an optical tomographic imaging apparatus for Fourier domain optical coherence tomography according to a fifth embodiment will be described with reference to FIGS. 5C and 5D.

The present embodiment differs from the fourth embodiment in a configuration of a spectroscope.

Otherwise, the configuration as an apparatus is similar to the fourth embodiment. Accordingly, descriptions of overlapping portions will be omitted.

Figure 5C:
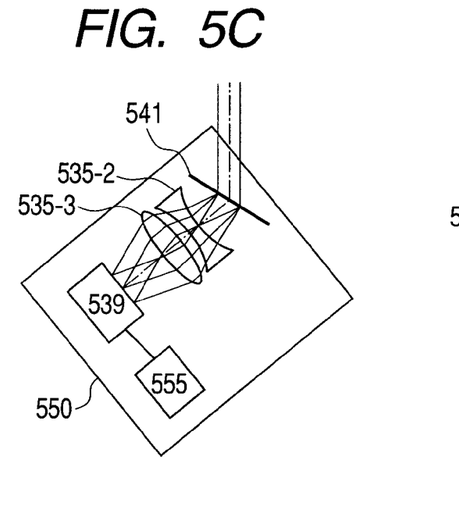
Figure 5D:
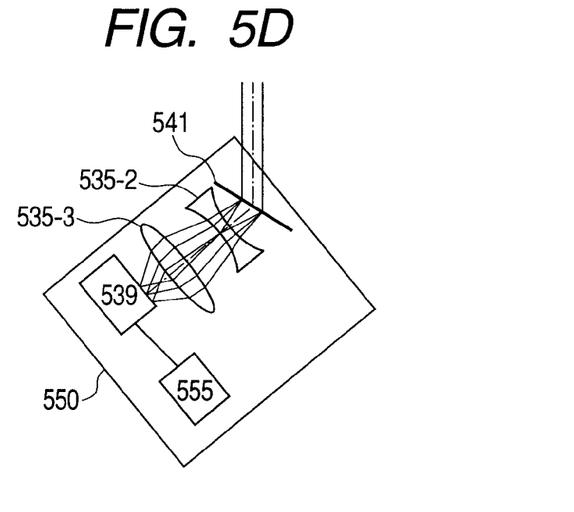

FIGS. 5C and 5D illustrate a spectroscope 550, a transmissive grating 541, and lenses 535-2 and 535-3. The two lenses are combined to form a zooming lens.

FIGS. 5C and 5D also illustrate a line camera 539, and a camera movement linear actuator 555 that moves the positions of the line camera 539 and the lenses 535-2 and 535-3 relative to each other.

Operations of the optical tomographic imaging apparatus according to the present embodiment in a low-resolution mode and in a high-resolution mode are the same as the third and fourth embodiments with the exception of a portion of the spectroscope.

In other words, adjustment of a depth of focus (DOF) range, adjustment of a gate position, and a procedure for acquiring a B-scan by varying a position of the depth of focus (DOF) range in stages in the high-resolution mode are also the same.

A light source similar to the first embodiment is used. The SLD has a wavelength of 840 nm and a bandwidth of 50 nm.

Using a variable expander, the beam diameter is set to 1 mm in the low-resolution mode and to 2 mm in the high-resolution mode. Therefore, values of a depth of focus (DOF) and a spot diameter value of each mode are the same as in the third and fourth embodiments.

Furthermore, optical paths of the measuring beam and the reference beam are also the same as in the first embodiment.

Operations around the spectroscope will now be described with reference to FIGS. 5C, 5D, 6C, 6D and 6E.

First, the state of the spectroscope in the low-resolution mode will be described.

In the same manner as in the first to third embodiments, a combined beam is guided to the spectroscope 550.

In the low-resolution mode, as illustrated in FIG. 5C, the lenses 535-2 and 535-3 are adjusted as a zooming lens to a long-focus state.

In addition, positions are adjusted by the camera movement linear actuator 555 so that a center of the line sensor inside the line camera 539 and an optical axis of the zooming lens made up of the lenses 535-2 and 535-3 are approximately consistent with each other.

Light separated into each wavelength by the transmissive grating 541 is condensed by the lenses 535-2 and 535-3.

The respective lenses 535-2 and 535-3 are adjusted as a zooming lens so that a 50 nm bandwidth light that forms an image on a line sensor 539-1 in the line camera 539 corresponds to the number of pixels in the line sensor.

Figure 6C:
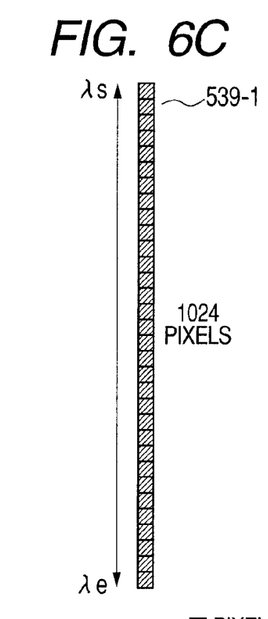

Specifically, as illustrated in FIG. 6C, an image is formed corresponding to the width of 1024 pixels of the line sensor inside the line camera 539.

FIG. 6C schematically illustrates the line sensor 539-1. Separated beams ranging from $\lambda_s$ (815 nm) to $\lambda_e$ (865 nm) form an image on the line sensor 539-1. This spectroscope state is similar to the fourth embodiment.

Next, the state of the spectroscope in the high-resolution mode will be described.

In the high-resolution mode, as illustrated in FIG. 5D, the lenses 535-2 and 535-3 are adjusted as a zooming lens to a short-focus state.

In addition, positions are adjusted by the camera movement linear actuator 555 so that the optical axis of the zooming lens made up of the lenses 535-2 and 535-3 is approximately consistent with the lower side of the line sensor inside the line camera 539 as depicted in FIG. 5D.

Figure 6D:
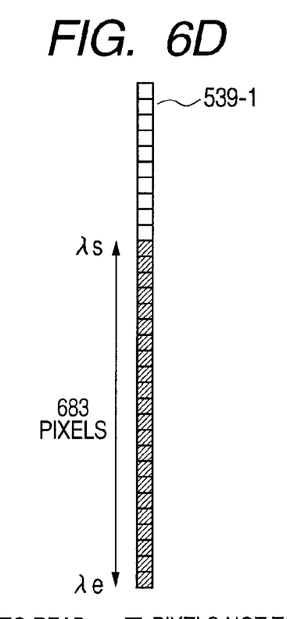

Specifically, as illustrated in FIG. 6D, the optical axis of the zooming lens is approximately consistent with a center of 683 pixels on the lower side of the line sensor 539-1 as depicted in the diagram.

Accordingly, light separated into each wavelength by the transmissive grating 541 or, in other words, light in a 50 nm range forms an image across a width corresponding to 683 pixels as illustrated in FIG. 6D. In this case, the line sensor 539-1 is provided in advance with a register to enable reading to be performed independently on the 683 pixels and, in this state, on 341 pixels outside of the image forming range.

Therefore, only the necessary 683 pixels of the line sensor 539-1 are read in the state illustrated in FIG. 6D in the high-resolution mode.

Accordingly, since the reading time of the line sensor can be reduced, imaging can be performed in an even shorter period of time.

Figure 6E:
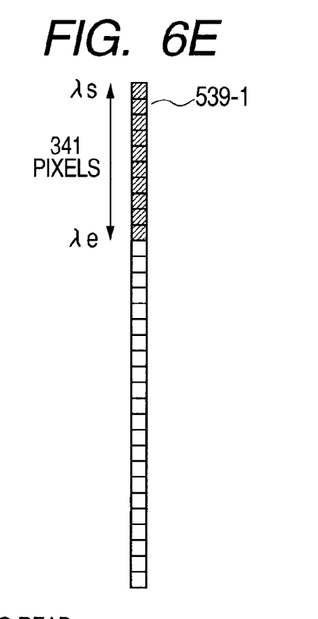

Furthermore, in the high-resolution mode, positions of the lenses 535-2 and 535-3 and the line camera may be adjusted to the image forming state illustrated in FIG. 6E.

In doing so, while the imaging optical distance is to correspond to 341 pixels (1.2 mm from expression (3)), such an imaging optical distance can be set when performing finer zone focusing to further reduce the reading time of the line sensor.

As described above, in the present embodiment, the absence of light quantity loss during imaging in the high-resolution mode using zone focusing results in a higher image contrast and a shorter imaging time. At the same time, by subjecting the line sensor to asymmetric region splitting and moving the image forming position of a zooming lens, the imaging optical distance can be diversely varied and the degree of freedom of selecting imaging speeds in the high-resolution mode can be increased.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-174928, filed Jul. 28, 2009, which is hereby incorporated by reference herein in its entirety.

What is claimed is:

1. An imaging method for acquiring a tomographic image of an eye based on a combined beam that combines a return beam from the eye irradiated by a measuring beam and a reference beam corresponding to the measuring beam, the imaging method comprising:
adjusting a beam diameter of the measuring beam;
dispersing the combined beam;
changing, by using a range changing unit including at least one lens, a size of a range on which the dispersed beam is to be irradiated based on the adjusted beam diameter;
detecting light from the range changing unit;
scanning the measuring beam on a retina of the eye with a vicinity of a cornea of the eye as a pivot; and
controlling the scanning such that a radiation position of the measuring beam in the retina is moved at a distance corresponding to the adjusted beam diameter.

2. An imaging apparatus for acquiring a tomographic image of an object based on a combined beam that combines a return beam from the object irradiated by a measuring beam and a reference beam corresponding to the measuring beam, the imaging apparatus comprising:
a beam diameter adjustment unit configured to adjust a beam diameter of the measuring beam; and
an electrically-powered stage configured to change a focusing position of the measuring beam at a distance shorter than a depth of focus based on the beam diameter adjusted by the beam diameter adjustment unit.

3. The imaging apparatus according to claim 2, wherein the object is an eye, and
wherein the imaging apparatus further comprises a scanning unit configured to scan the measuring beam on a retina of the eye with a vicinity of a cornea of the eye as a pivot.

4. The imaging apparatus according to claim 3, further comprising a control unit configured to control the scanning unit such that a radiation position of the measuring beam in the retina is moved at a distance corresponding to the beam diameter adjusted by the beam diameter adjustment unit.

5. The imaging apparatus according to claim 2, further comprising a Central Processing Unit (CPU), wherein the CPU performs a process of acquiring tomographic images before and after the focusing changing unit changes the focusing position of the measuring beam, and combining the acquired tomographic images.

6. An imaging method for acquiring a tomographic image of an object based on a combined beam that combines a return beam from the object irradiated by a measuring beam and a reference beam corresponding to the measuring beam, the imaging method comprising:
adjusting a beam diameter of the measuring beam; and
changing a focusing position of the measuring beam at a distance shorter than a depth of focus based on the adjusted beam diameter.

7. The imaging method according to claim 6, wherein the object is an eye, and
wherein the method further comprises scanning the measuring beam on a retina of the eye with a vicinity of a cornea of the eye as a pivot.

8. The imaging method according to claim 7, further comprising controlling the scanning such that a radiation position of the measuring beam in the retina is moved at a distance corresponding to the adjusted beam diameter.

9. The imaging method according to claim 6, further comprising:
performing a process of acquiring tomographic images before and after the changing of the focusing position of the measuring beam; and
combining the acquired tomographic images.

10. A non-transitory computer-readable storage medium storing a program for causing a computer to execute an imaging method for acquiring a tomographic image of an object based on a combined beam that combines a return beam from the object irradiated by a measuring beam and a reference beam corresponding to the measuring beam, the imaging method comprising:
adjusting a beam diameter of the measuring beam; and
changing a focusing position of the measuring beam at a distance shorter than a depth of focus based on the adjusted beam diameter.

11. An imaging apparatus for acquiring a tomographic image of an object based on a combined beam that combines a return beam from the object irradiated by a measuring beam and a reference beam corresponding to the measuring beam, the imaging apparatus comprising:
a plurality of apertures with different diameters configured to adjust a beam diameter of the measuring beam by selecting one of the plurality of apertures and inserting the one of the plurality of apertures into an optical path of the measuring beam; and
an electrically-powered stage configured to change a focusing position of the measuring beam at a distance shorter than a depth of focus based on the beam diameter adjusted by the plurality of apertures.

12. An imaging apparatus for acquiring a tomographic image of an object based on a combined beam that combines a return beam from the object irradiated by a measuring beam and a reference beam corresponding to the measuring beam, the imaging apparatus comprising:
a positive lens and a negative lens configured to adjust a beam diameter of the measuring beam by varying the spacing between the positive lens and the negative lens; and
an electrically-powered stage configured to change a focusing position of the measuring beam at a distance shorter than a depth of focus based on the beam diameter adjusted by the positive lens and the negative lens.

* * * * *